United States Patent [19]

Kaneta et al.

[11] Patent Number: 5,066,599

[45] Date of Patent: Nov. 19, 1991

[54] SILICON CRYSTAL OXYGEN EVALUATION METHOD USING FOURIER TRANSFORM INFRARED SPECTROSCOPY (FTIR) AND SEMICONDUCTOR DEVICE FABRICATION METHOD USING THE SAME

[75] Inventors: Hiroshi Kaneta, Kawasaki; Shuichi Muraishi, Tokyo, both of Japan

[73] Assignees: Fujitsu Limited, Kawasaki; Jeol, Ltd., Tokyo, both of Japan

[21] Appl. No.: 555,702

[22] Filed: Jul. 23, 1990

[30] Foreign Application Priority Data

Jul. 27, 1989 [JP] Japan .................... 1-194700

[51] Int. Cl.$^5$ ............................................ H01L 21/00
[52] U.S. Cl. .................................... 437/7; 437/8; 437/10; 250/341; 250/339; 156/601
[58] Field of Search ............... 437/7, 8, 10; 250/341, 250/339; 156/601

[56] References Cited

U.S. PATENT DOCUMENTS

| 3,868,185 | 2/1975 | Genzel . | |
| 4,342,616 | 8/1982 | Elliott et al. | 156/601 |
| 4,429,047 | 1/1984 | Jastrzebski | 156/601 |
| 4,590,574 | 5/1986 | Edmonds et al. | 250/339 |
| 4,862,000 | 8/1989 | Kubota | 250/341 |

FOREIGN PATENT DOCUMENTS

| 065490 | 3/1984 | Japan . |
| 61-17031 | 1/1986 | Japan . |

OTHER PUBLICATIONS

Mead, D. G., Solid State Technology, 11/81, p. 71.
Ohsawa, A., Appl. Phys. Lett. 36(2) 1/15/80, p. 147.
Shimura, F. et al., Applied Physics Letters 38(11) pp. 867–870, 6/1/87.
American National Standard "Standard Test Method for Substitutional Atomic Carbon Contest of Silicon by Infrared Absorption", pp. 523–524, F123–70T, Jan. 1976.
Cotten-Solal, G. et al., Applied Phys. Letters, vol. 19, #10, p. 436, 11/15/71.
Kachmarsky, J. et al., Applied Optics, vol. 15, No. 3, 3/76, p. 708.
IBM, TDB, vol. 23, No. 4, Sep. 1980, p. 1389.
Humecki, H. J., Solid State Technology, 4/85, pp. 309–313.

*Primary Examiner*—Brian E. Hearn.
*Assistant Examiner*—Gordon V. Hugo
*Attorney, Agent, or Firm*—Armstrong, Nikaido, Marmelstein, Kubovcik & Murray

[57] ABSTRACT

A silicon crystal evaluation method includes the step of measuring, at room temperature, an intensity of an oxygen impurity infrared absorption peak of each of a plurality of silicon crystals at a wavenumber of $1107 \pm 3 cm^{-1}$. Each of the silicon crystals contains oxygen impurities, the silicon crystals including an evaluated silicon crystal having an unknown thermal history and reference silicon crystals having respective known thermal histories. The second step is to measure, at a temperature equal to or lower than 10K, an intensity of an oxygen impurity infrared absorption peak of each of the silicon crystals at a predetermined wavenumber. A third step is to calculate a first peak intensity ratio between the intensity of the oxygen impurity infrared absorption peak of each of the silicon crystals at $1107 \pm cm^{-1}$ and the intensity of the oxygen impurity infrared absorption peak at the predetermined wavenumber. The fourth step is to calculate a first difference between the first peak intensity ratio of the evaluated silicon crystal and a corresponding, second peak intensity ratio obtained when all oxygen impurities are isolated point lattice defects. The fifth step is to calculate a second difference between the first peak intensity ratio of each of the reference silicon crystals and the second peak intensity ratio. The sixth step is to evaluate the unknown thermal history of the evaluated silicon crystal from reference data which defines a relationship between the second difference and the known thermal histories.

25 Claims, 13 Drawing Sheets

WAVENUMBERS (Cm⁻¹)

SILICON CRYSTAL OXYGEN EVALUATION METHOD USING FOURIER TRANSFORM INFRARED SPECTROSCOPY (FTIR) AND SEMICONDUCTOR DEVICE FABRICATION METHOD USING THE SAME

BACKGROUND OF THE INVENTION

The present invention generally relates to a silicon crystal evaluation method, and more particularly to a silicon crystal evaluation method directed to predicting how much oxygen precipitates are formed during a specific heat treatment for a device using a silicon crystal which has an unknown thermal history and to discriminating silicon crystals having an identical oxygen impurity concentration and having different thermal histories from each other. Further, the present invention is directed to providing a silicon crystal evaluation method capable of accurately obtaining the concentration of isolated interstitial oxygen impurities in a silicon crystal and evaluating precipitated oxygen impurities in a silicon crystal on the basis of a standard with respect to the state (morphology) and content of precipitated impurities (precipitate defects). Moreover, the present invention is concerned with a method of fabricating a semiconductor integrated circuit device using the silicon crystal evaluation method.

There is known a phenomenon in which oxygen impurities contained in a silicon crystal in a thermally unstable morphology (a supersatulated state, for example) are morphologically changed during a heat treatment in semiconductor device processing. Conventionally, it is required to precisely predict the above-mentioned phenomenon by a crystal evaluation which is carried out before the semiconductor device fabrication process. Oxygen precipitates contained in a silicon crystal have the function of absorbing impurity atoms, such as Fe, Ni and Co, which are not desirable to be contained in a device active region of the silicon crystal. This function is known as the gettering effect.

Conventionally, there is no evaluation method directed to evaluating morphological differences of oxygen impurities contained in as-grown crystals before the semiconductor device fabrication process and knowing how many oxygen precipitation nuclei are contained before the fabrication process. Slight morphological differences of oxygen impurities contained in (as grown) crystals cause great differences in the amount of precipitated oxygen after the heat treatment during the fabrication process and thus cause remarkable problems frequently.

Oxygen impurities can exist in various states due to various thermal histories of crystals even when the concentration of oxygen impurities in silicon crystals obtained immediately after the crystal production is the same. It should be noted that the above has been known only experimentially. In other words, there is no special measurement means for quantitatively measuring various states of oxygen impurities contained in crystals.

Although it is possible to obtain the concentration of all oxygen atoms contained in an as-grown silicon crystal by using a conventional room temperature infrared absorption spectra analysis, it is impossible to identify morphological differences of oxygen precipitation nuclei in the as-grown silicon crystal, particularly due to the thermal history during silicon crystal production processing. That is, it is impossible to specify the starting point of the oxygen precipitation phenomenon arising from a heat treatment (annealing, for example) during the device fabrication process, or initial morphological differences of oxygen impurities contained in crystals. For the above-mentioned reason, even when crystals having an identical oxygen concentration is subjected to the same heat treatment during device processing, the content of oxygen precipitation nuclei is different for different crystals due to the respective thermal histories thereof during the crystal production process.

As is well known, the aforementioned gettering effect depends on the total amount (number) of oxygen precipitate defects. The gettering effect is zero when there is no precipitate defect. On the other hand, a large degree of the gettering effect is expected when there is a large number of oxygen precipitate defects. Further, there is a variety of morphology of oxygen precipitates. Thus, the gettering effect depends on morphology of precipitates (related to the structure and size) as well as the content (concentration) of precipitates related to individual states thereof.

The inventors have been proposed a silicon crystal evaluation method by Japanese Laid-Open Patent Application No. 63-167907. Except for this silicon crystal evaluation method, the inventors do not know a method for detecting a morphological change of oxygen impurities (formation of oxygen precipitation nuclei and growth thereof) contained in an as-grown crystal. This change depends on the thermal history of an as-grown crystal or a light heat treatment equivalent to the thermal history of the as-grown crystal.

Conventionally, it is possible to evaluate a great morphological change of oxygen impurities contained in a crystal resulting from a special thermal history or a heavy heat treatment by a photoluminescence method (see M. Tajima et al., Appl. Phys. Lett., 43, 1983, pp.274). However, the photoluminescence method is not capable of detecting a morphological change of oxygen impurities (formation of oxygen precipitation nuclei) due to a relatively light heat treatment. By using an infrared absorption spectra analysis, it is also possible to detect a morphological change of oxygen impurities at a time when oxygen precipitation is in an advanced stage (see F. Shimura et al., Appl. Phys. Lett., 46, 1985, pp. 941). Except for this case, it is presently impossible to detect oxygen precipitation nuclei (see F. shimura et al., Appl. Phys. Lett., 46, 1985, pp. 941, or M. Tajima et al., Appl. Phys. Lett., 51, 1983, pp. 2247).

In addition, it is said that the room-temperature infrared absorption spectra method does not provide a large amount of evaluation information and many species of evaluation information. The aforementioned Japanese application No. 63-167907 is not capable of measuring, at a temperature equal to or lower than 10K, absorption spectral peaks of L1, L2, L3 and M which are some peaks to be measured. In addition, the peak intensity depends on temperature greatly at temperatures higher than 10K, and thus the measurement temperature must be set within a narrow allowable temperature range equal to 0.05K. However, it is very difficult to regulate the measurement temperature.

As has been mentioned hereinbefore, there is no simple silicon crystal evaluation method directed to predicting oxygen precipitation. Conventionally, oxygen precipitation is predicted by measuring the content of all oxygen impurities by means of the aforementioned room-temperature infrared spectra analysis. According to the room-temperature infrared spectra analysis, the concentration of all oxygen impurities is quantitatively measured by utilizing a room-temperature $1106\pm1$ cm$^{-1}$ peak which is an absorption peak resulting from oxygen atoms in a silicon crystal. As will be described later, this method does not accurately provide the concentration of oxygen precipitates.

It will be noted that the aforementioned differences of the oxygen precipitation content arise from the fact that there is a variety of morphology of oxygen impurities contained in a silicon crystal even if the oxygen concentration is constant and that conventional methods, particularly the room-temperature infrared spectra analysis, are not capable of measuring morphological differences of oxygen impurities in silicon crystals.

As described above, there is experientially known the phenomenon in which oxygen precipitation is based on conditions for producing crystals, especially the thermal histories during the crystal production process and there is a variety of morphology (states) of oxygen impurities in crystals (which are respectively starting points of the device processing) due to the differences in thermal histories during the crystal production process. However, there is nothing directed to easily obtaining physical values which reflect the differences of morphology of oxygen impurities contained in silicon crystals.

The aforementioned infrared absorption spectra analysis utilizing the room-temperature $1106\pm1$ cm$^{-1}$ peak cannot provide accurate physical values which reflect the morphological differences of oxygen impurities in silicon crystals due to the following reasons.

A description will now be given of a variety of morphology of oxygen impurities contained in silicon crystals in order to facilitate understanding the problems of the room-temperature infrared absorption spectra analysis. A typical morphology (state) of oxygen impurities contained in silicon crystals is isolated interstitial oxygen atoms which are located in a mutually isolated state. Hereinafter, this is represented by Oi. Oi generates an impurity infrared absorption peak at a wavenumber of $1106\pm1$ cm$^{-1}$ at room temperature. This peak is called an Oi peak. Normally, in a (as-grown) state before precipitates are formed, almost all oxygen impurities exist in the form of isolated interstitial oxygen impurities (Oi). Thus, it is possible to quantitatively obtain the oxygen concentration [Oi] of as-grown crystal by measuring the intensity of an Oi peak as shown in FIG. 1. On the other hand, precipitated oxygen impurities (oxygen precipitate defects) generate the Oi peak no longer. Thus, the intensity of the Oi peak decreases by a level corresponding to the content of oxygen precipitate defects formed from some of all the oxygen impurities [Oi]. By using a decreased peak intensity level, it is possible to predict how much oxygen impurities are precipitated or how much precipitate defects exist.

However, this method has the following problems. As shown in FIG. 2, a state of precipitate defects (called P1 state) generate an impurity infrared absorption peak (called P1 peak) at a wavenumber (approximately $1106\pm1$ cm$^{-1}$) which is almost the same as that of the Oi peak. The P1 peak overlaps the Oi peak so that they are not separated from each other. As a result, a decreased intensity of the Oi peak due to the formation of oxygen precipitates is not evaluated correctly. If the entire overlap of the P1 peak and the Oi peak is considered as the Oi peak without noticing the presence of the P1 peak, the oxygen precipitate defects in the P1 state are neglected so that the content of all precipitate defects (the amount of precipitated Oi) is underestimated. Currently, it is very difficult to separate the P1 peak from the Oi peak by the room-temperature infrared absorption spectra analysis. From this viewpoint, at present, errors introduced by this analysis cannot help being accepted. That is, the current precipitate defect evaluation method cannot indicate the accurate content of precipitate defects.

Further, the conventional precipitate defect evaluation method has a serious problem described below. There are many morphological differences of precipitate defects in view of the structure and the size thereof. It is generally considered that the gettering effect depends, to some extent, on the total content of precipitate defects (the precipitated Oi content). In addition, the gettering effect greatly depends on what state of precipitates is contained and how much the precipitates are contained. Conventionally, it is possible to observe the shape and/or size of precipitate defects by chemically etching the precipitate defects and measuring the etched precipitate defects by a microscope. However, the size, shape or density of precipitate defects change by the etching condition. For example, by changing the concentration or composition of an etchant or etching time, precipitates which have not been observed (counted) appear, or precipitates which have been observed disappear. Moreover, the number of precipitates is counted by the naked eye. Thus, there is a problem that the counted results greatly depend on who counts the precipitates. In addition, there are fine differences related to the structure of precipitate defects, which cannot be observed by the naked eye. In some cases, the fine differences considerably affect the gettering effect.

SUMMARY OF THE INVENTION

It is an object of the present invention to provide a silicon crystal evaluation method in which the above-mentioned problems are eliminated.

A more specific object of the present invention is to provide a silicon crystal evaluation method capable of predicting how much oxygen precipitates are generated by a heat treatment during device processing.

Another object of the present invention is to provide a silicon crystal evaluation method capable of accurately obtaining the interstitial oxygen impurity concentration in a heat-treated silicon crystal.

Yet another object of the present invention is to provide a silicon crystal evaluation method capable of evaluating precipitated impurities in a heat-treated silicon crystal on the basis of a standard with respect to morphology and content of precipitated impurities.

The above-mentioned objects of the present invention are achieved by a silicon crystal evaluation method comprising the steps of:

a) measuring, at room temperature, an intensity of an oxygen impurity infrared absorption peak of each of a plurality of silicon crystals at a wavenumber of $1107\pm3$ cm$^{-1}$, each of the silicon crystals containing oxygen impurities, the silicon crystals including an evaluated silicon crystal having an unknown thermal history and reference silicon crystals having respective known thermal histories;

b) measuring, at a temperature equal to or lower than 10K, an intensity of an oxygen impurity infrared absorption peak of each of the silicon crystals at a predetermined wavenumber;

c) calculating a first peak intensity ratio between the intensity of the oxygen impurity infrared absorption peak of each of the silicon crystals at $1107\pm3$ cm$^{-1}$ and the intensity of the oxygen impurity infrared absorption peak at the predetermined wavenumber;

d) calculating a first difference between the first peak intensity ratio of the evaluated silicon crystal and a corresponding, second peak intensity ratio obtained when all oxygen impurities are isolated point lattice defects;

e) calculating a second difference between the first peak intensity ratio of each of the reference silicon crystals and the second peak intensity ratio; and f) evaluating the unknown thermal history of the evaluated silicon crystal from reference data which defines a relationship between the second difference and the known thermal histories.

The aforementioned objects of the present invention are also achieved by a silicon crystal evaluation method comprising the steps of:

a) measuring a crystal defect infrared absorption spectrum in a wavenumber range between 900 cm$^{-1}$ and 1300 cm$^{-1}$;

b) measuring an intensity of an infrared absorption peak appearing at a predetermined wavenumber when oxygen impurities are isolated point lattice defects; and c) calculating a concentration of isolated interstitial oxygen impurities from an intensity of the crystal defect infrared absorption spectrum and the intensity of the infrared absorption peak measured by the step b).

A further object of the present invention is to provide a semiconductor device fabrication method using the above-mentioned silicon crystal evaluation method.

This object of the present invention is achieved by a semiconductor device fabrication method comprising the steps of:

a) evaluating a thermal history of a silicon wafer;

b) heating the silicon wafer on the basis of the thermal history evaluated by the step a); and c) introducing an impurity having a conduction type opposite to that of the silicon wafer into the silicon wafer so that a PN-type junction is formed in the silicon wafer, wherein the step a) comprises:

a-1) measuring, at room temperature, an intensity of an oxygen impurity infrared absorption peak of each of a plurality of silicon crystals at a wavenumber of $1107\pm3$ cm$^{-1}$, each of the silicon crystals containing oxygen impurities, the silicon crystals including an evaluated silicon crystal which is the silicon wafer having an unknown thermal history and reference silicon crystals having respective known thermal histories;

a-2) measuring, at a temperature equal to or lower than 10K, an intensity of an oxygen impurity infrared absorption peak of each of the silicon crystals at a predetermined wavenumber;

a-3) calculating a first peak intensity ratio between the intensity of the oxygen impurity infrared absorption peak of each of the silicon crystals at $1107\pm3$ cm$^{-1}$ and the intensity of the oxygen impurity infrared absorption peak at the predetermined wavenumber;

a-4) calculating a first difference between the first peak intensity ratio of the evaluated silicon crystal and a corresponding, second peak intensity ratio obtained when all oxygen impurities are isolated point lattice defects;

a-5) calculating a second difference between the first peak intensity ratio of each of the reference silicon crystals and the second peak intensity ratio; and a-6) evaluating the unknown thermal history of the evaluated silicon crystal from reference data which defines a relationship between the second difference and the known thermal histories.

BRIEF DESCRIPTION OF THE DRAWINGS

Other objects, features and advantages of the present invention will become apparent from the following detailed description when read in conjunction with the accompanying drawings, in which.

DESCRIPTION OF THE PREFERRED EMBODIMENTS

Figure 1:
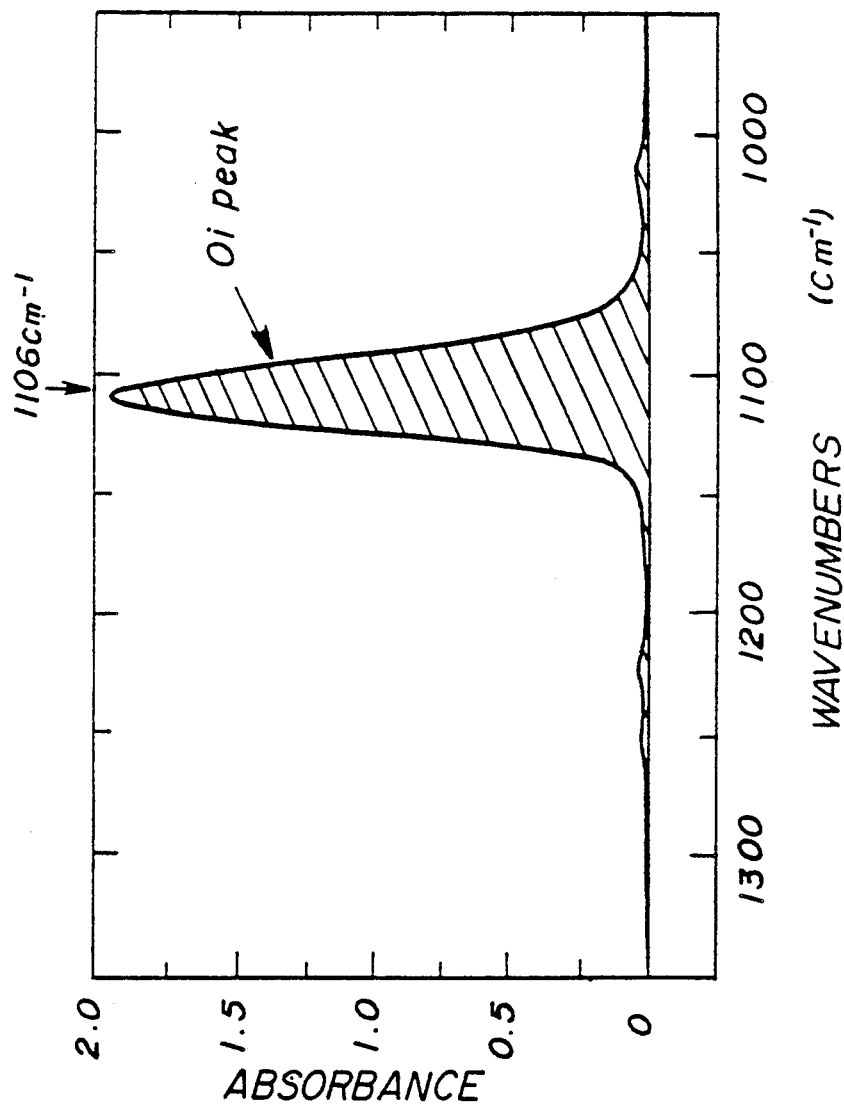
FIG. 1 is a graph illustrating a room-temperature infrared absorption spectra for an as-grown silicon crystal containing interstitial oxygen impurities.

According to the present invention, the intensity levels of the following three oxygen impurity infrared absorption peaks of a silicon crystal containing oxygen impurities are measured. First, the intensity I(RT 1107) of an oxygen impurity infrared absorption peak observed at a wavenumber of $1107\pm3$ cm$^{-1}$ at room temperature (between 0° C. and 40° C.) is measured. Second, the intensity I(HeT 1206) of an oxygen impurity infrared absorption peak observed at a wavenumber of $1206\pm3$ cm$^{-1}$ and a temperature equal to or lower than 10K, such as the liquid helium temperature (hereafter also referred to as HeT) is measured. Third, the intensity I(HeT 1749) of an oxygen impurity infrared absorption peak observed at a wavenumber of 1749±3 cm$^{-1}$ and a temperature equal to or lower than 10K, such as the HeT, is measured. Then, the ratio of peak intensity levels is calculated. When using the three peaks, the ratio, I(RT 1107): I(HeT 1206): I(HeT 1749) is calculated. The subsequent step is to calculate the difference (first difference) between the peak intensity ratio thus calculated and the peak intensity ratio obtained in a case where all oxygen impurities in a silicon crystal are isolated from each other. On the other hand, the peak intensity ratio is calculated for a plurality of crystals having known thermal histories. Then reference data indicating the differences (second difference) between the peak intensity ratios for the known thermal histories and the thermal histories is obtained. By using the reference data thus calculated, it is possible to evaluate the thermal history of the silicon crystal being considered. It is preferable that the above-mentioned three peaks be used for obtaining the thermal history of silicon crystal. However, the present invention is not limited to the above. It is also possible to use two of the three peaks. For example, the thermal history can be obtained by using the ratio I(RT 1107): I(HeT 1206) or I(RT 1107): I(HeT 1749). The peaks at wavenumbers of 1206±3 and 1749±3 cm$^{-1}$ are very sensitive to infrared rays.

While measuring the intensity I(HeT 1206) and the intensity I(HeT 1749), the measurement temperature is set equal to or lower than 10K, preferably in the range of 1.5K (precise measurement) to 6K (simplicity of measurement). It is now assumed that the peak intensity ratio of an as-grown crystal is generally represented as follows:

$$I(RT\ 1107): I(HeT\ 1206): I(HeT\ 1749) = [a]:[b]:[c] \tag{1}$$

As will be described later, the peak intensity ratio is slightly different for different thermal histories during the crystal production process. When the as-grown silicon crystal is subjected to a heat treatment for producing precipitates, starting from the as-grown state, some oxygen impurities morphologically change from minute precipitation nuclei to precipitates of a macro size. Thus, the peak intensity levels are decreased by x, y and z. That is, the peak intensity ratio is changed as follows.

$$[a]-x:[b]-y:[c]-z \tag{2}$$

In this case, the individual relative decrease amounts x/[a], y/[b] and z/[c] are not equal to each other but as follows.

$$x/[a] \leq y/[b] \leq z/[c] \tag{3}$$

The formula (3) is found out by a low-temperature high-resolution measurement and logically analyzed by the inventors. The details of the above measurement and analysis will be described in detail later. It should be noted that the inventors found out that even if a heat treatment causes no change in the peak intensity I(RT 1107) (x=0), changes in the peak intensity I(HeT 1206) and the peak intensity I(HeT 1749) are observed (0<y, z; 0<y/[b]<z/[c]). That is, the peak intensity decreases by a value corresponding to oxygen atoms which change to precipitation nuclei and precipitates when morphological changes of oxygen impurities, such as precipitation nuclei formation and precipitation nuclei growth, occur. A decreasing value of the peak intensity I(HeT 1206) is greater than that of the peak intensity I(RT 1107), and a decreasing value of the peak intensity I(HeT 1749) is greater than that of the peak intensity I(HeT 1206). The present invention is due to the above fact found by the inventors.

It is now assumed that the peak intensity ratio obtained when all oxygen impurity atoms are spaced apart from each other so that they are isolated from each other are written as a:b:c. It will be noted that when oxygen impurity atoms are isolated from each other, there is no interaction therebetween. Oxygen atoms in an as-grown silicon crystal having an oxygen concentration equal to or less than 15 ppm, all oxygen atoms are in an isolated defect state. When all the oxygen impurity atoms are of the isolated defect state, the following relationship is obtained.

$$I(RT\ 1107):I(HeT\ 1206):I(HeT\ 1749) = a:b:c \tag{4}$$

According to the measurements conducted by the inventors, the ratio defined by formula (4) is as follows.

$$a:b:c = 1:0.307:0.0992$$

The following formula is related to the peak intensity ratio a:b:c of a silicon crystal in which oxygen impurities have been changed to the isolated defect state by a heat treatment directed to cancelling its thermal history in which typically the temperature is set equal to or higher than 1250° C. for one to two hours, $$a = [a] + X$$

$$b = [b] + Y \tag{5}$$

$$c = [c] + Z$$

where X>0, Y>0 and Z>0. It will be noted that X, Y and Z are increased values of peak intensity due to the fact that oxygen atoms contained in the as-grown silicon crystal in the state of precipitation nucleus defects change to the isolated defect state. Formula (5) is rewritten as follows.

$$[a] = a(1-X/a)$$

$$[b] = b(1-Y/b) \tag{6}$$

$$[c] = c(1-Z/c)$$

Thus, the following formula is obtained.

$$[a]:[b]:[c] = a(1-X/a):b(1-Y/b):c(1-Z/c) \tag{7}$$

It will be noted that X/a, Y/b and Z/c are contributed by oxygen atoms which was originally contained in the silicon crystal in the state of precipitation nucleus defects. As described previously, a relative decreased level of the peak intensity due to the formation of precipitation nuclei has the following relationship.

$$X/a < Y/b < Z/c$$

As a result, the peak intensity ratio on the right side of the formula (7) deviates from the peak intensity ratio a:b:c. Thus, it becomes possible to predict the content (concentration) of precipitation nucleus defects contained in the as-grown silicon crystal by measuring the peak intensity ratio [a]:[b]:[c] and calculating a deviation from the peak intensity ratio, a:b:c.

The inventors found out, by the experiments, the fact that the thermal history of crystal is noticeably reflected on the two HeT oxygen impurity infrared absorption peaks at $1206\pm3$ cm$^{-1}$ and $1749\pm3$ cm$^{-1}$. A description will now be given of the experiments conducted by the inventors.

The typical thermal history of crystal affecting oxygen precipitation is a low-temperature thermal history. The low-temperature thermal history is modeled by heating a crystal at a temperature of approximately 700° C. The content of oxygen precipitates formed in a low-temperature heat treated crystal when executing a high-temperature heat treatment, is much different from the content of oxygen precipitates which are formed in a crystal which has not been subjected to the low-temperature heat treatment when the latter crystal is subjected to the same high-temperature heat treatment. From this viewpoint, oxygen precipitation nuclei depend on the low-temperature thermal history (heat treatment). However, as described previously, the presence of oxygen precipitation nuclei has not yet been expressed by physical values. In the experiments, samples were cut out from an identical portion of one as-grown crystal ingot. The cutout samples were respectively subjected to various low-temperature heat treatments in a nitrogen atmosphere. After that, the absorption peak intensity levels I(RT 1107), I(HeT 1206) and I(HeT 1749) were measured. In the measurements, the wavenumber resolution was 0.25 cm$^{-1}$. The relationship between the examined samples and the heat treatments (reference data) is shown in Table 1. The measured intensity levels I(RT 1107), I(HeT 1206) and I(HeT 1749) shown in Table 1 are relative values when the intensity levels of the three peaks I(RT 1107), I(HeT 1206) and I(HeT 1749) of an as-grown silicon crystal are respectively assumed to be 100%.

TABLE 1

| Sample | Heat Treatment | I(RT 1107) | I(HeT 1206) | I(HeT 1749) |
|---|---|---|---|---|
| S1 | none (as-grown) | 100% | 100% | 100% |
| S2 | 700° C., 16 h | 100 | 97 | 94 |
| S3 | 700° C., 64 h | 95 | 93 | 93 |
| S4 | 700° C., 128 h | 77 | 73 | 68 |
| S5 | 1250° C., 2 h | 101 | 103 | 104 |
| S6 | 450° C., 64 h + 700° C., 16 h | 90 | 82 | 79 |
| S7 | 450° C., 64 h + 700° C., 64 h | 80 | 78 | 76 |
| S8 | 450° C., 64 h + 700° C., 128 h | 11 | 3 | 3 |

Figure 3:
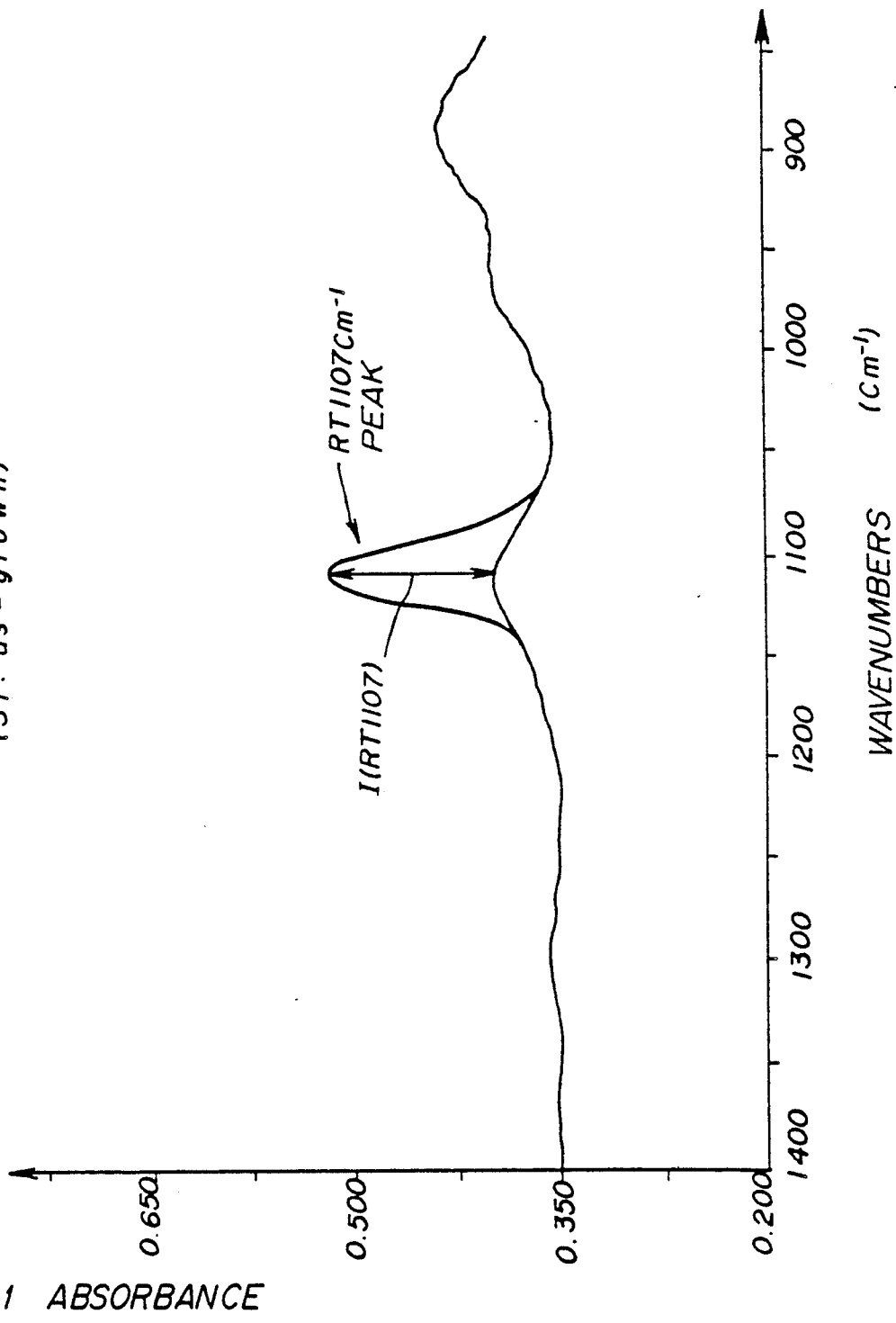
FIG. 3 is a graph illustrating a room temperature infrared absorption spectrum of an as-grown silicon crystal (sample S1) containing oxygen impurities.
Figure 4:
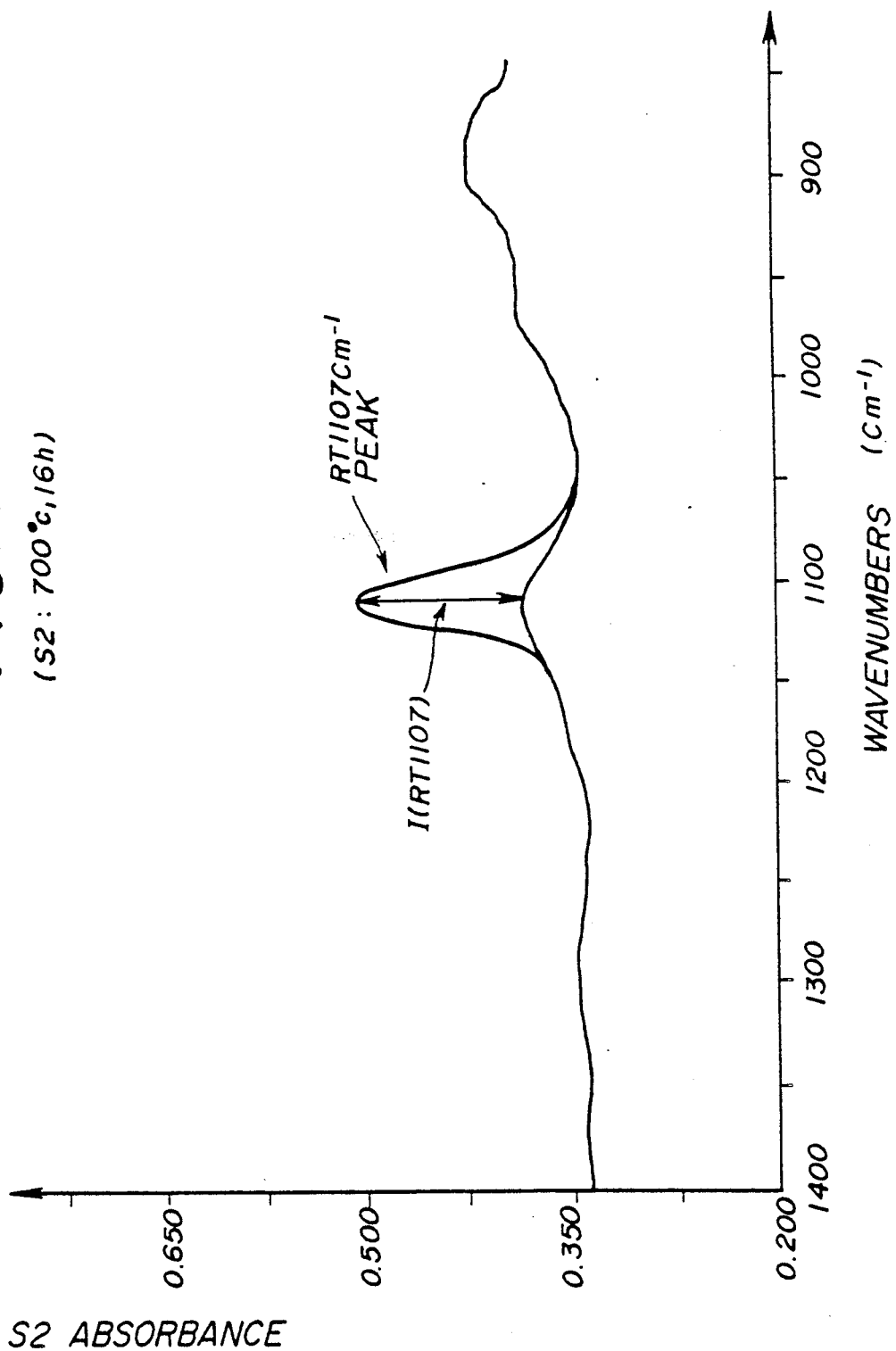
FIG. 4 is a graph illustrating a room temperature infrared absorption spectrum of a silicon crystal (sample S2) which contains oxygen impurities and has been subjected to a 700° C. 16 h heat treatment.

FIGS. 3 and 4 are graphs illustrating absorption spectra around the RT 1107 cm$^{-1}$ peaks of the samples S1 and S2 in Table 1, respectively. In detail, FIG. 3 is a graph of an infrared absorption spectrum of an as-grown silicon crystal containing oxygen impurities which is measured at room temperature RT. The graph of FIG. 3 shows a 1107 cm$^{-1}$ absorption peak due to the presence of oxygen impurities. The intensity of the 1107 cm$^{-1}$ absorption peak, I(RT 1107), is measured based on a base line obtained by overlapping an absorption spectrum of an as-grown silicon crystal having no oxygen impurity in an area excluding the 1107 cm$^{-1}$ absorption peak. In FIG. 3, the base line corresponds to a curve drawn at a lower portion of the the 1107 cm$^{-1}$ absorption peak. FIG. 4 is a graph of an RT infrared absorption spectrum of a silicon crystal which contains oxygen impurities and which has been subjected to a heat treatment at 700° C. for 16 hours. The as-grown silicon crystal before the heat treatment has the same thermal history as that related to FIG. 3.

It is possible to almost completely fit each other the two spectra shown in FIGS. 3 and 4 within the illustrated frequency range. This means that the precipitation nuclei formed by the low-temperature thermal history (heat treatment at 700° C. for 16 h) are not observed at the RT 1107 cm$^{-1}$ absorption peak. The curves shown on the lower side of the absorption spectra shown in FIGS. 3 and 4 are base lines used for calculating the intensity I(RT 1107) and obtained by overlapping the spectra of the silicon crystal containing no oxygen which are observed at the area excluding the 1107 cm$^{-1}$ absorption peak.

Figure 5:
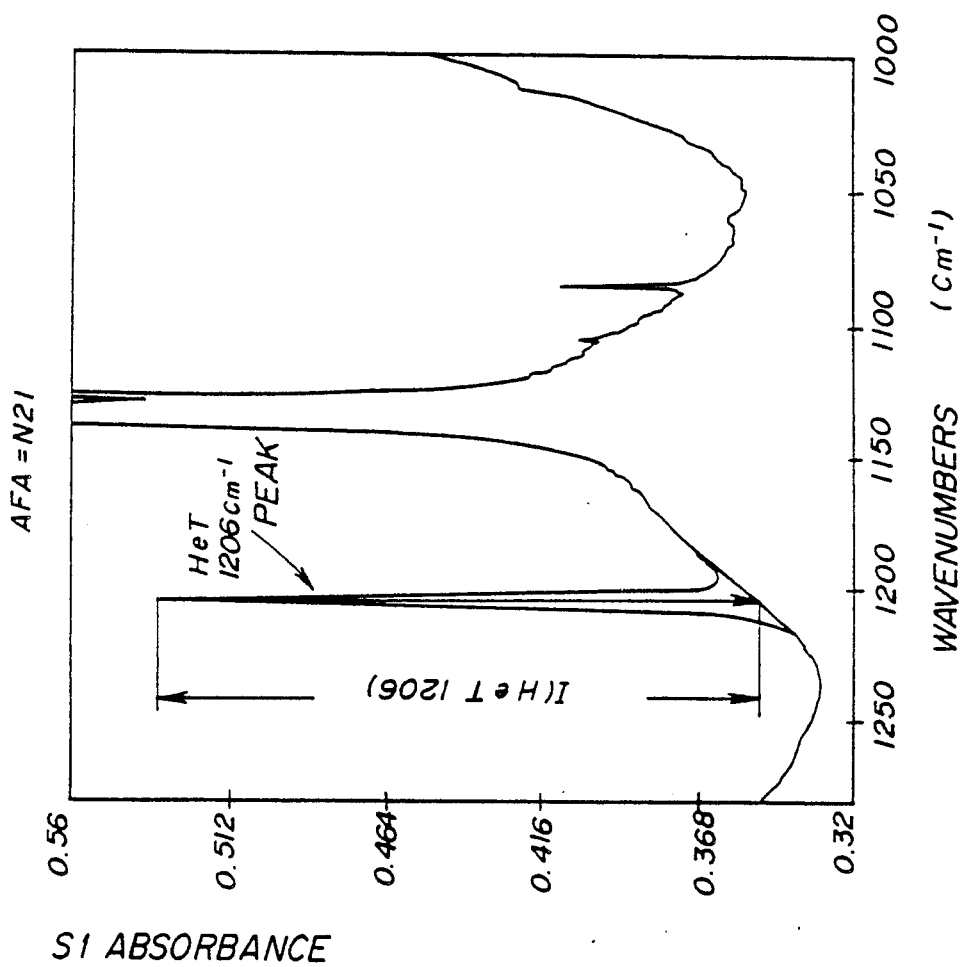
FIG. 5 is a graph illustrating a liquid helium temperature infrared absorption spectrum of the as-grown silicon crystal (sample S1) containing oxygen impurities.
Figure 6:
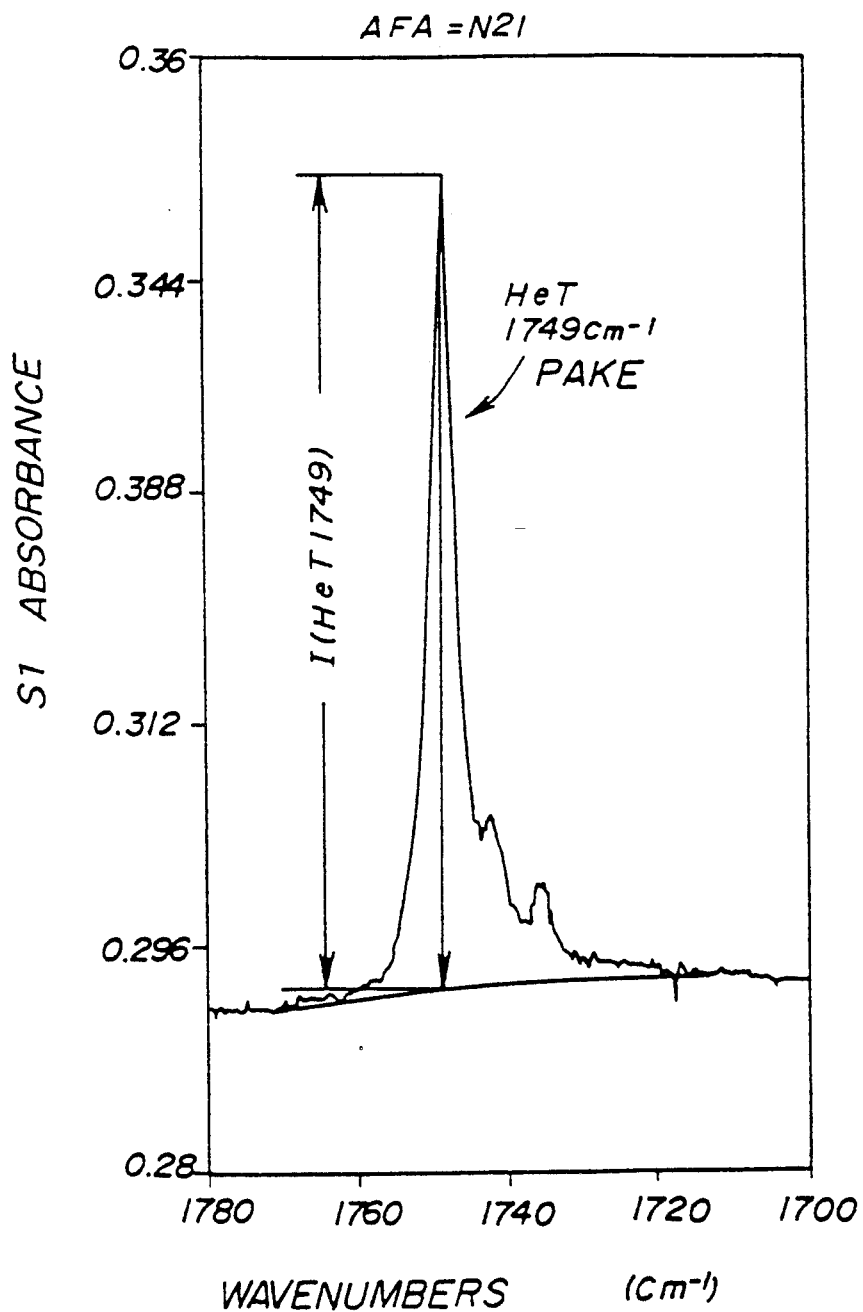
FIG. 6 is a graph illustrating a liquid helium temperature infrared absorption spectrum of the as-grown silicon crystal (sample S1) containing oxygen impurities.

On the other hand, FIGS. 5 and 6 are graphs of HeT (liquid helium temperature) absorption peaks of the sample S1 at 1206 cm$^{-1}$ and 1749 cm$^{-1}$, respectively. In detail, FIG. 5 is a graph of a HeT infrared absorption spectrum of an as-grown silicon crystal containing oxygen impurities. The peak at 1206 cm$^{-1}$ results from the presence of oxygen impurities. Other peaks at 1085 cm$^{-1}$ and 1136 cm$^{-1}$ also result from the presence of oxygen impurities. The intensity I(HeT 1206) of the oxygen impurity infrared absorption peak is measured with respect to a base line obtained by superimposing an absorption spectrum of a silicon crystal containing no oxygen impurities in an area excluding the oxygen impurity infrared absorption peak. In FIG. 5, the above-mentioned base line is a curve depicted on the lower side of the oxygen impurity infrared absorption peak. FIG. 6 is a graph of a HeT infrared absorption spectrum of an as-grown silicon crystal containing oxygen impurities. The peak appearing at 1749 cm$^{-1}$ results from the presence of oxygen impurities. Other peaks at 1743 cm$^{-1}$ and 1736 cm$^{-1}$ also result from the presence of oxygen impurities. The intensity I(HeT 1749) of the oxygen impurity infrared absorption peak is measured with respect to a base line obtained by overlapping an absorption peak of a silicon crystal having no oxygen impurities in an area excluding the oxygen impurity infrared absorption peak. In FIG. 6, this base line is a curve shown on the lower side of the oxygen impurity infrared absorption peak.

The absorption peaks shown in FIGS. 5 and 6 reflect the effect of the low-temperature heat treatment (700° C., 16 h). As shown in Table 1, the intensity I(HeT 1206) is decreased to 97% of that of the as-grown crystal by the low-temperature heat treatment. Similarly, the intensity I(HeT 1749) is decreased to 94% of that of the as-grown crystal by the low-temperature heat treatment. That is, the effects brought by the low-temperature heat treatment (700° C., 16 h) are not reflected on the RT 1107 cm$^{-1}$ peak at all, while remarkably reflected on the HeT 1206 cm$^{-1}$ and HeT 1749 cm$^{-1}$ absorption peaks with decreases in the peak intensity. In addition, a decrease in the peak intensity I(HeT 1749) is greater than a decrease in the peak intensity I(HeT 1206). These experimental results are generalized by the aforementioned formula (3). The experimental results will easily be understood by rewriting Table 1 into a graph which has the horizontal axis representative of the condition of the low-temperature heat treatment and the vertical axis representative of the intensity levels I(RT 1107), I(HeT 1206) and I(HeT 1749).

Figure 7:
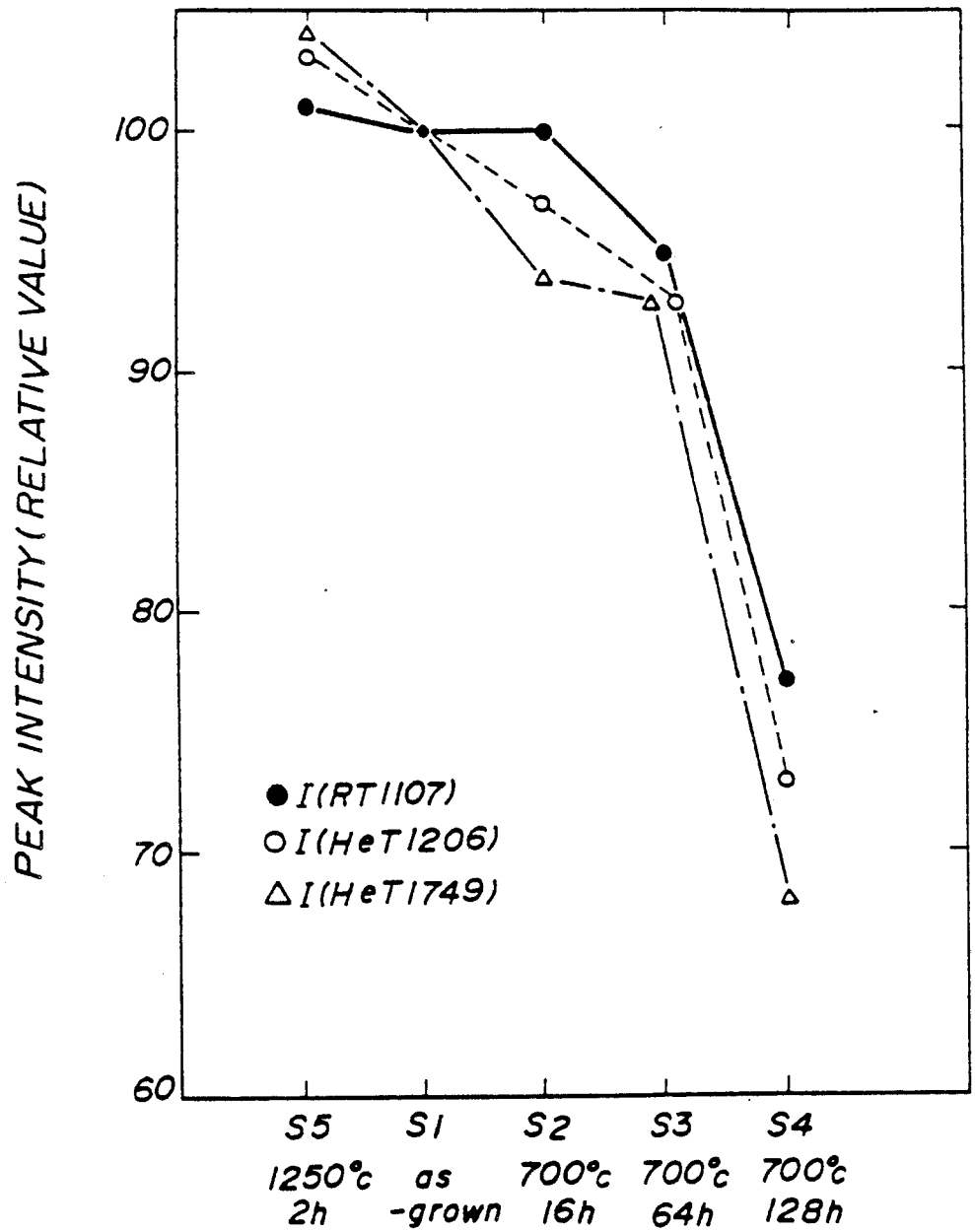
FIG. 7 is a graph illustrating changes in peak intensity levels (relative values) I(RT 1107), I(HeT 1206) and I(HeT 1749) due to a heat treatment.

FIG. 7 is a graph illustrating changes in the peak intensity levels due to various heat treatments carried out for some of the samples S1-S5. The peak intensity levels are illustrated by relative values when the intensity levels of the three peaks I(RT 1107), I(HeT 1206) and I(HeT 1749) of an as-grown silicon crystal are respectively assumed to be 100%. The intensity levels shown in FIG. 7 are also shown in Table 1. It will be noted that the peak intensity level corresponds to a peak height or a peak area.

Figure 8:
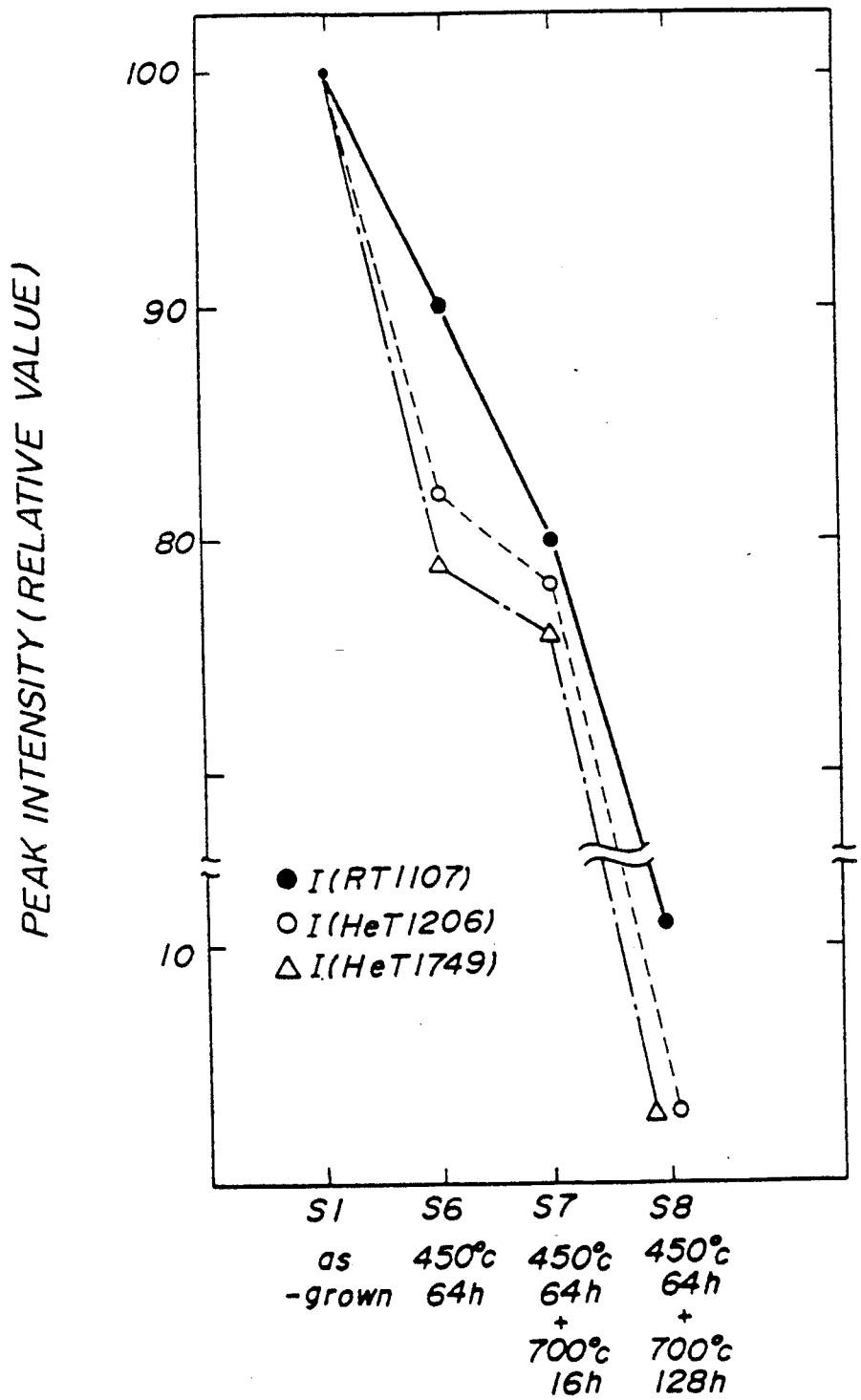
FIG. 8 is a graph illustrating changes in peak intensity levels (relative values) I(RT 1107), I(HeT 1206) and I(HeT 1749) due to a heat treatment.

FIG. 8 is a graph illustrating changes in the peak intensity levels due to various heat treatments carried out for the samples S1 and S6-S8. The peak intensity levels are illustrated by relative values when the intensity levels of the three peaks I(RT 1107), I(HeT 1206) and I(HeT 1749) of an as-grown silicon crystal are 100%. The intensity levels shown in FIG. 8 are also shown in Table 1.

In FIGS. 7 and 8, the formula (3) is always satisfied. That is, when a morphological change of oxygen impurities caused by the low-temperature heat treatment, such as the formation of precipitation nuclei or the growth thereof is caused, the peak intensity levels decrease by a level corresponding to the content of oxygen impurities which are changed to precipitation nuclei or precipitates. In this case, a decrease in I(HeT 1206) is greater than that in I(RT 1107) and a decrease in I(HeT 1749) is greater than that in I(HeT 1206). In addition, even if no change in I(RT 1107) is observed, changes in I(HeT 1206) and I(HeT 1749) are observed.

The peak intensity levels, I(RT 1107), I(HeT 1206) and I(HeT 1749) shown in Table 1 are relative values when the peak intensity levels of the as-grown crystal are respectively assumed to be 100%. When representing the peak intensity levels by using a common scale related to the peak intensity, such as an absorption coefficient and by calculating the ratio between the peak intensity levels, the aforementioned formula is obtained.

$$I(RT\ 1107):I(HeT\ 1206):(HeT\ 1749)=[a]:[b]:[c]$$

The sample S5 in Table 1 has been subjected to the aforementioned high-temperature heat treatment for cancelling the thermal history. Thus, all oxygen impurities contained in the sample S5 are considered to be in the isolated defect state (isolated interstitial oxygen impurities). That is, the sample S5 is expressed by the aforementioned formula (4) as follows.

$$I(RT\ 1107):I(HeT\ 1206):I(HeT\ 1749)=a:b:c \qquad (8)$$

On the other hand, the following is obtained from Table 1.

$$a:b:c=1.01[a]:1.03[b]:1.04[c] \qquad (9)$$

Thus, the following is obtained.

$$[a]:[b]:[c]$$

$$=a/1.01:b/1.03:c/1.04 \qquad (10)$$

$$=a(1-0.01):b(1-0.03):c(1-0.04) \qquad (11)$$

Comparing this formula with the formula (6), the following relationship is obtained.

$$X/a=0.01$$

$$Y/b=0.03$$

$$Z/c=0.04 \qquad (12)$$

The formula (12) means that the peak intensity ratio [a]:[b]:[c] of the as-grown crystal deviates from the by about X/a, Y/b, Z/c, respectively. The reference data shown in Table 1 are only parts of the experimental results obtained by the inventors. In the experiments, other as-grown crystals each having an oxygen concentration equal to or greater than 30 ppm (old SATM conversion) were subjected to the high-temperature heat treatment for cancelling the thermal history. The inventors found out the fact that the peak intensity ratio [a]:[b]:[c] of each as-grown crystal also deviates from the ratio for the isolated defect state by the following values.

$$X/a=0.00-0.02$$

$$Y/b=0.02-0.09 \qquad (13)$$

$$Z/c=0.04-0.09$$

These deviations result from the fact that oxygen exists in the state of a composite defect due to the thermal history. Further the deviations are caused by the low-temperature heat treatment (thermal history) which forms oxygen precipitation nuclei, as described previously. As a result, the fact that the peak intensity ratio [a]:[b] and [c] of the as-grown crystal deviates from the ratio a:b:c in the isolated defect state are primary based on the presence of oxygen precipitation nuclei contained in the as-grown crystal. Thus, it becomes possible to predict the content (concentration) of oxygen precipitation nuclei contained in an as-grown crystal by measuring the peak intensity ratio [a]:[b]:[c] of the as-grown crystal and calculating a deviation from the ratio a:b:c for the isolated defect state.

The phenomenon that all the peak intensity levels I(RT 1107), I(HeT 1206) and I(HeT 1749) are decreasing during the time when oxygen atoms in the isolated defect state are changed to precipitation nuclei and these precipitation nuclei grow to precipitates, will simply be understood from the fact that all the absorption peaks thereof result from oxygen in the isolated defect state. However, the experimental fact that the peak intensity ratio I(RT 1107):I(HeT 1206):I(HeT 1749) deviates from the ratio a:b:c transcends intuitive understanding. The above experimental fact will be understood on the basis of theoretical studies by the inventors related to oxygen impurity infrared absorption due to the presence of oxygen in the isolated defect state (see H. Yamada-Kaneta et al., 15th Int. Conference on Defects in Semiconductors (Budapest, 1988), Material Science Forum, Vol.38–41, 1989, pp.637 and C. Kaneta et al., 15th Int. Conference on Defects in Semiconductors (Budapest, 1988), Material Science Forum, Vol.38–41, 1989, pp.323).

Figure 9:
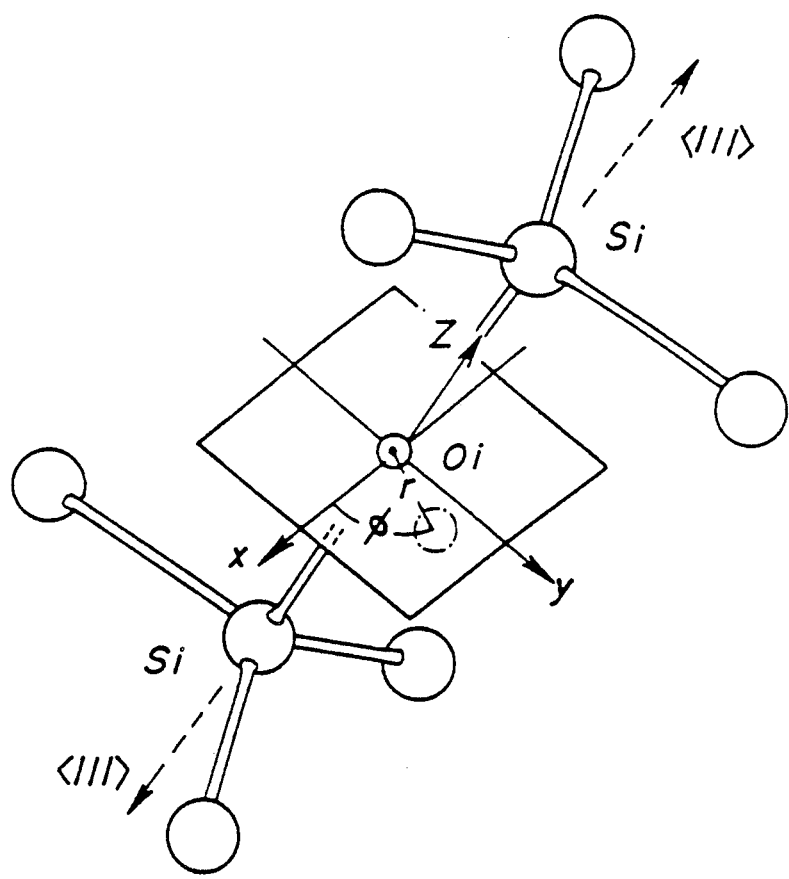
FIG. 9 is a diagram illustrating an orientation state of an isolated oxygen impurity (Oi) contained in a silicon crystal lattice.
Figure 10:
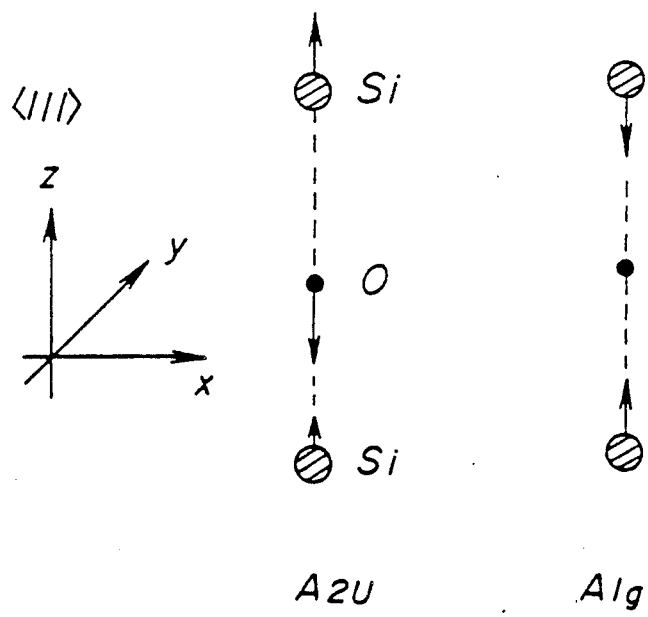
FIG. 10 is a diagram illustrating impurity vibration modes described in accordance with the orthogonal coordinate axes shown in FIG. 9.

Referring to FIG.9, there is illustrated a configuration of an isolated oxygen impurity (Oi) in a silicon crystal lattice. FIG. 10 is a diagram illustrating impurity vibration modes using the orthogonal coordinate axes shown in FIG.9. As shown in FIGS. 9 and 10, an oxygen atom in the isolated defect state occupied at an interstitial position on Si-Si bonding axis along the [111] direction of the original silicon crystal lattice. The orthogonal coordinate axes are employed by describing the impurity lattice vibrations caused by the presence of Oi. In FIG. 10, there are illustrated an $A_{2u}$ type vibration mode and an $A_{1g}$ type vibration mode. In addition, there is a unharmonic mode of Oi due to a displacement parallel to the (x, y) plane (see FIG. 9). In this case, impurity vibration modes resulting from the following locally existing impurity lattice vibrations appear:

1) unharmonic vibration due to the degree of freedom of the (x, y) motion of Oi;

2) $A_{2u}$ type vibration containing a z-displacement of Oi and a displacement of Si atoms adjacent thereto; and 3) $A_{1g}$ type vibration consisting of a displacement of Si atoms adjacent to Oi.

Although other impurity vibration modes appear, a description thereof will be omitted because they are not needed to describe the present consideration. These impurity vibration modes are bonded to each other by unharmonic bonding. When infrared light is projected onto the unharmonic bonding, it is possible to observe not only an impurity infrared absorption due to only the above-mentioned modes 1) and 2) but also a multi-quantum excitation infrared absorption caused by exiting the modes 1), 2) and 3) at the same time. The RT 1107 cm$^{-1}$ absorption results from only the aforementioned mode 2), and the HeT 1206 cm$^{-1}$ absorption is a multi-quantum excitation infrared absorption due to the fact that the modes 1) and 2) are simultaneously excited. The HeT 1749 cm$^{-1}$ absorption is a multi-quantum excitation infrared absorption due to the fact that the modes 2) and 3) are simultaneously excited. Although the three absorption peaks result from oxygen (Oi) in the same isolated defect state, the (bonding) modes contributing to the absorption peaks are different from the different absorption peaks. Thus, when oxygen atoms become close to each other during the formation of precipitation nuclei, each mode is affected by other oxygen atoms closed to the originally related oxygen atoms. As a result, one or more modes among the aforementioned three modes disappear from the mode that is most sensitive to the influence of other oxygen atoms (one or more modes are changed to other modes having a completely different excitation frequency). Since the sensitivity to other oxygen atoms which become close to the originally related oxygen atoms is different for different modes, all the intensity levels I(RT 1107), I(ReT 1206) and I(HeT 1749) are not reduced uniformly, and thus the ratio I(RT 1107):I(ReT 1206):I(HeT 1749) deviates from the ratio a:b:c during the time when precipitation nuclei are formed or precipitation nuclei grow to precipitates.

In the experiments conducted by the inventors, the ratio a:b:c for a large number of crystals in which all oxygen impurities are in the isolated defect state was accurately measured. Then, the most likely ratio was calculated from a large amount of data related to the measured ratio by using the least mean square method. In the experiments, the inventors used as-grown crystals, each having an oxygen concentration equal to or less than 25 ppm (old ASTM conversion) and crystals obtained by subjecting as-grown crystals each having an oxygen concentration equal to or greater than 25 ppm (old ASTM conversion) to a high-temperature heat treatment for cancelling the thermal history. These crystals are considered that all oxygen impurities contained therein are in the isolated defect state. The ratio a:b:c is normalized by "a" so that it is written as 1:/b/:/c/. That is, $$/b/=b/a, \text{ and } /c/=c/a \quad 1:/b/:/c/=a/a:b/a:c/a \quad (14)$$

Next, the ratio [a]:[b]:[c] of as-grown crystals each having an oxygen concentration equal to or greater than 31 ppm. By normalizing this ratio by [a], the following is obtained.

$$1:/[b]/:/[c]/=[a]/[a]:[b]/[a]:[c]/[a] \quad (15)$$

Then, using the following formulas $$/[b]/=/b/(1-/y/) \quad /[c]/=/c/(1-/z/) \quad (16)$$

the values /y/ and /z/ were calculated for each of the as-grown samples. The values /y/ and /z/ of each sample were as follows.

$$/y/=0.00-0.04$$

$$/z/=0.00-0.05$$

Then, these as-grown samples were subjected to an oxygen precipitation heat treatment in which they were heated at 700° C. for 4 hours and then at 1100° C. for 5 hours. After that, the correlation in (/y/, /z/) and precipitation content between the heat-treated as-grown samples having an almost identical initial oxygen concentration were investigated. The experimental results show that a large content of precipitates is formed in a sample having large values of /y/ and /z/. This means that samples which have almost the same oxygen concentration but have large values of /y/ and /z/ have a high ratio of oxygen existing in the precipitation nuclei. Thus, it is understood that such crystals generate a large oxygen precipitation content during precipitation heat treatment.

By obtaining /y/ and /z/ in the above-mentioned way, it is possible to determine whether or not a crystal being considered is easier to form oxygen precipitates than other crystals each having an almost identical initial oxygen concentration, that is, whether or not the crystal of interest has a high precipitation density.

It is preferable that temperature control be carried out by monitoring a 1128 cm$^{-1}$ infrared absorption peak and ascertaining that this peak does not appear during the procedure for measuring the 1206+3 cm$^{-1}$ and 1749+3 cm absorption peaks at a temperature equal to or lower than 10K. The 1128 cm$^{-1}$ peak appears at a temperature of about 7K and becomes most intense at about 35K. It is possible to regulate the measurement temperature at temperatures equal to or lower than about 7K so that the 1128 cm$^{-1}$ peak does not appear. It will be noted that the peak intensity is almost the same at temperatures equal to or lower than 7K.

A description will now be given of a second preferred embodiment of the present invention which is directed to separating the aforementioned Oi peak and P1 peak from each other. Infrared absorption peaks due to isolated interstitial oxygen appear at wavenumbers of 515, 1106, 1225 and 1720 cm$^{-1}$ at room temperature. The intensity ratio between these peaks is always constant. That is, although the proportionality coefficients are different, the intensities of these peaks are proportional to an interstitial oxygen concentration. It appears from the principle that the aforementioned problem in that it is impossible to quantitatively measure precipitated oxygen on the basis of the Oi peak intensity because the Oi peak at 1106 cm$^{-1}$ overlaps the P1 peak, will be eliminated by using peaks, such as 515 cm$^{-1}$ peak and 1720 cm$^{-1}$ peak, which do not superimpose the precipitate 1106 cm$^{-1}$ peak. However, the peaks which do not overlap the 1106 cm$^{-1}$ peak due to the precipitates are not suitable for the quantitative measurement of the interstitial oxygen concentration because of actual reasons such that these peaks do not exhibit sufficient intensity levels and that it is difficult to separate these peaks from an absorption due to the host crystal lattice.

According to the second embodiment of the present invention, absorptions peaks at 1206 cm$^{-1}$ and 1748 cm$^{-1}$ measured at HeT are used. These peaks result from isolated interstitial oxygen. The ratio of the HeT 1206 cm$^{-1}$ peak to the RT 1106 cm$^{-1}$ peak (Oi peak) is always constant, and the ratio of the HeT 1748 cm$^{-1}$ peak to the RT 1106 cm peak is also always constant. That is, although the values of the proportionality coefficients are different for the above two ratios, the intensity of each of the RT 1106 cm$^{-1}$ peak, the HeT 1206 cm$^{-1}$ peak and the HeT 1748 cm$^{-1}$ peak is proportional to the isolated interstitial oxygen concentration. According to our experimental results, the proportionality coefficient between the RT 1106 cm$^{-1}$ peak intensity and the isolated interstitial oxygen concentration is equal to 9.6, that is, (isolated interstitial oxygen
concentration)=9.6×(RT 1106 cm$^{-1}$ peak
intensity)         (17)

In this case, the HeT 1206 cm$^{-1}$ peak intensity and the HeT 1748 cm$^{-1}$ peak intensity are written by the following conversion relationships.

(isolated interstitial oxygen
concentration)=31.27×(HeT 1206 cm$^{-1}$ peak
intensity)         (18)

(isolated interstitial oxygen
concentration)=96.80×(HeT 1748 cm$^{-1}$ peak
intensity)         (19)

It will be noted that in the above formulas (17)–(19), the isolated interstitial oxygen concentration has a unit of ppm and the unit of peak intensity is the peak absorption coefficient cm$^{-1}$. The 1206 cm$^{-1}$ and 1749 cm$^{-1}$ peaks at HeT have intensity levels sufficient to the quantitative measurement of isolated interstitial oxygen concentration, and have very small peak half-widths. Thus, it is easy to separate these peaks from the host crystal lattice absorption (measurement of spectral difference).

Figure 2:
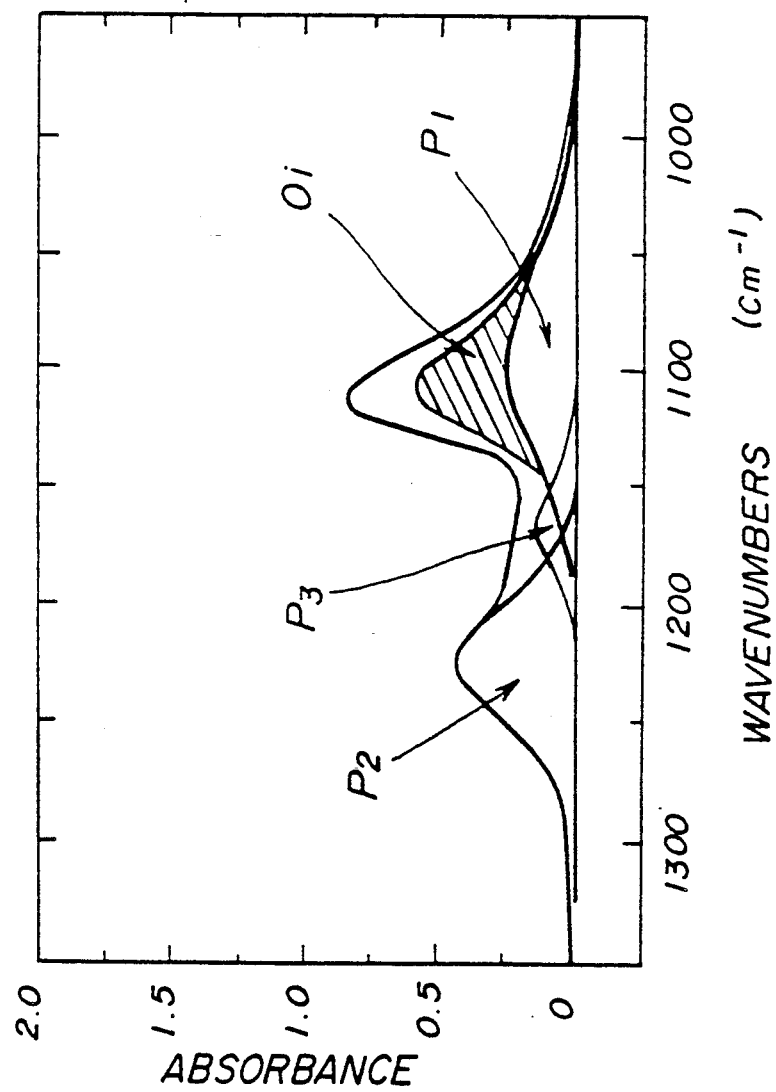
FIG. 2 is a graph illustrating room-temperature impurity absorption spectra for a silicon crystal containing interstitial oxygen impurities (Oi) and precipitated defects) which has been subjected to a heat treatment.

Further, according to the second embodiment of the present invention, it is possible to classify precipitate defects into individual states and quantitatively measure the classified into precipitate defects. According to the study by the inventors, the precipitate defects are classified three categories on the basis of the infrared absorptions. The first category is related to the aforementioned P1 peak. The second category is related to a P2 peak appearing at about 1220 cm$^{-1}$. The third category is related to a P3 peak appearing at an intermediate portion between the above two peaks. Hereinafter, these peaks are respectively referred to as P1 defect, P2 defect and P3 defect. The P2 defect is cristobalite having a composition of SiO$_2$. The RT infrared absorption of a crystal containing precipitate defects and isolated interstitial oxygen is measured so that as shown in FIG. 2, the P1 peak, the P2 peak and P3 peak superimpose the 1106 cm$^{-1}$ Oi peak at 1106 cm$^{-1}$. It becomes possible to obtain the interstitial oxygen concentration from the measured HeT 1206 cm$^{-1}$ peak intensity by using the aforementioned formula (17). When applying the obtained interstitial oxygen concentration to formula (17), it becomes possible to subtract the Oi peak intensity (hatched portion in FIG. 2) from the superimposed peak intensity. Further, when utilizing the fact that the P1 peak has right-side and left-side portions which are symmetrical with each other (this is known from a crystal containing only p1 peak), it becomes possible to separate the P1 peak from the remaining P2 and P3 peaks. It is possible to know the details of the entire precipitate defects from the intensity ratio between the P1 peak and the P2 peak. According to our experiment, the area intensity of the P1 peak per a unit oxygen concentration (the area intensity of the P1 peak obtained when all 1 ppm interstitial oxygen is changed to P1 defects) is always constant and approximately equal to 1.42 cm$^{-1}$/ppm. The wavenumber of the P2 peak is altered depending on the formation process (heat treatment condition) and crystal. Thus, it becomes possible to identify a difference in the structure of the P2 defect.

Figure 11:
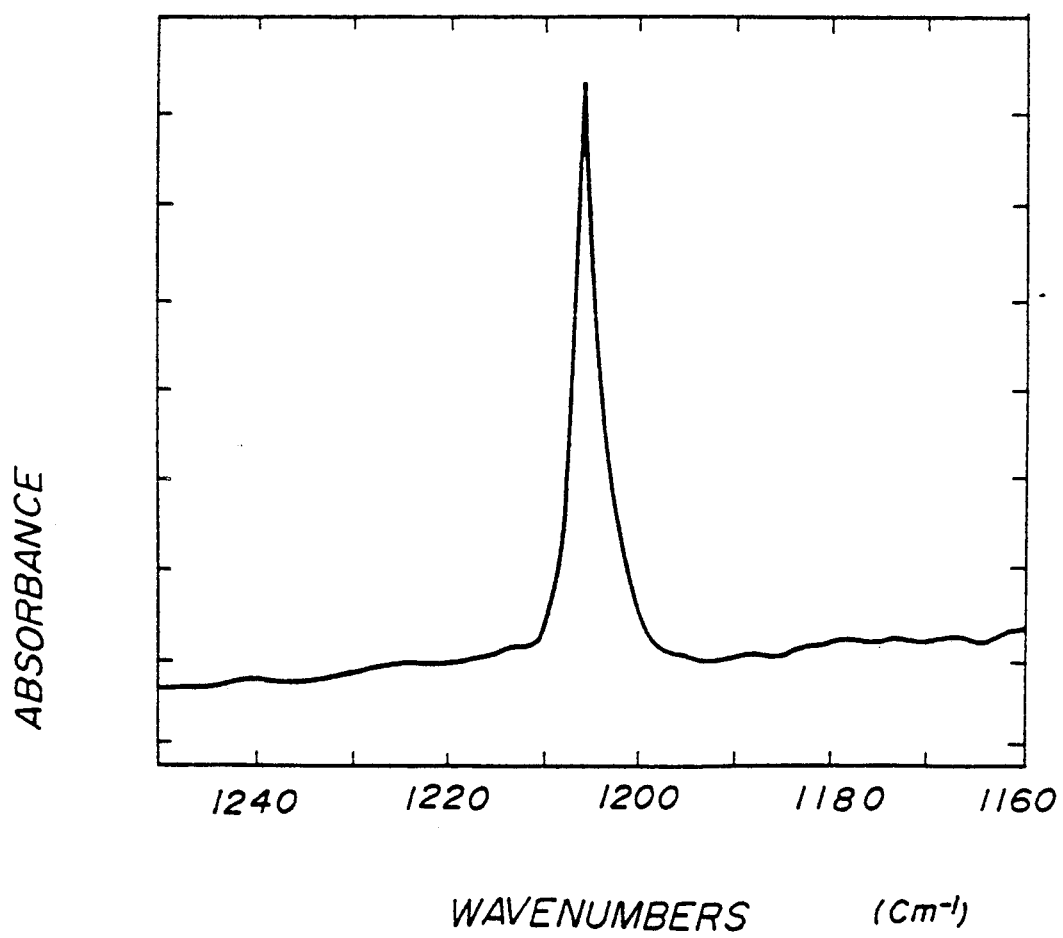
FIG. 11 is a graph illustrating a 1206 cm$^{-1}$ absorption peak due to interstitial oxygen impurity contained a heat-treated silicon crystal measured at the liquid helium temperature.

A description will now be given of the measurement of the isolated interstitial oxygen impurity concentration and the evaluation of precipitate defects with reference to FIGS. 1, 2 and 11. As has been described previously, FIG. 1 is the oxygen impurity infrared absorption spectrum of the as-grown silicon crystal measured at room temperature. It can be seen from FIG. 1 that only the 1106 cm$^{-1}$ peak (Oi peak) due to isolated interstitial oxygen impurities appears. FIG. 2 is the graph of the impurity infrared absorption spectrum obtained after the above as-grown crystal is subjected to a heat treatment in which it is heated at 700° C. for 8 hours and then 1000° C. for 2 hours. FIG. 11 is a graph of an isolated interstitial oxygen impurity absorption peak of the above heat-treated crystal measured at liquid helium temperature (HeT).

By inserting the peak intensity level shown in FIG. 1 into the formula (17), the concentration of all oxygen impurities in the as-grown crystal being considered is equal to 32.6 ppm. By inserting the peak intensity level shown in FIG. 11 into the formula (18), the concentration of isolated interstitial oxygen is equal to 11.3 ppm. The difference equal to 21.3 ppm (=32.6−11.3) indicates precipitate defects which are formed by the heat treatment. It can be seen from the formula (17) that the remaining 11.3 ppm isolated interstitial oxygen contributes to a peak portion indicated by the hatched areas shown in FIG. 2. By subtracting this portion from the overlapping peak and turning up a low-wavenumber portion of the remaining spectrum toward the high-wavenumber side, the P1 peak is obtained. Further, by subtracting the P1 peak intensity, the P2 and P3 peaks are obtained. It can be seen from this subtraction result that the area intensity of the P1 peak is equal to 17.3 cm$^{-2}$. As has been described previously, the area intensity of the P1 peak is always constant and approximately equal to 1.42 cm$^{-2}$/ppm. From this, it can be seen that 12.2 ppm isolated interstitial oxygen is changed to P1 defects. Thus, it is concluded that the remaining 9.1 ppm isolated interstitial oxygen is changed to the P2 and P3 defects. In summary, 21.3 ppm isolated interstitial oxygen out of 32.6 ppm interstitial oxygen originally contained in the crystal is changed to precipitate defects by the the heat treatment, and 10.0 ppm interstitial oxygen out of 21.3 ppm interstitial oxygen is changed to the P1 defects, and the remaining 11.3 ppm is changed to the P2 and P3 defects.

A description will now be given of a semiconductor device fabricating method which uses the aforementioned silicon crystal evaluation method according to the present invention. Silicon wafers of semiconductor devices are presented by slicing silicon ingots. A silicon ingot is produced by controlling solidification of a silicon melt. Thus, an ingot portion initially produced has a thermal history different from that of a lately produced ingot portion. According to the present invention, a heat treatment for compensating for this thermal history difference is carried out for silicon wafers.

Figure 12:
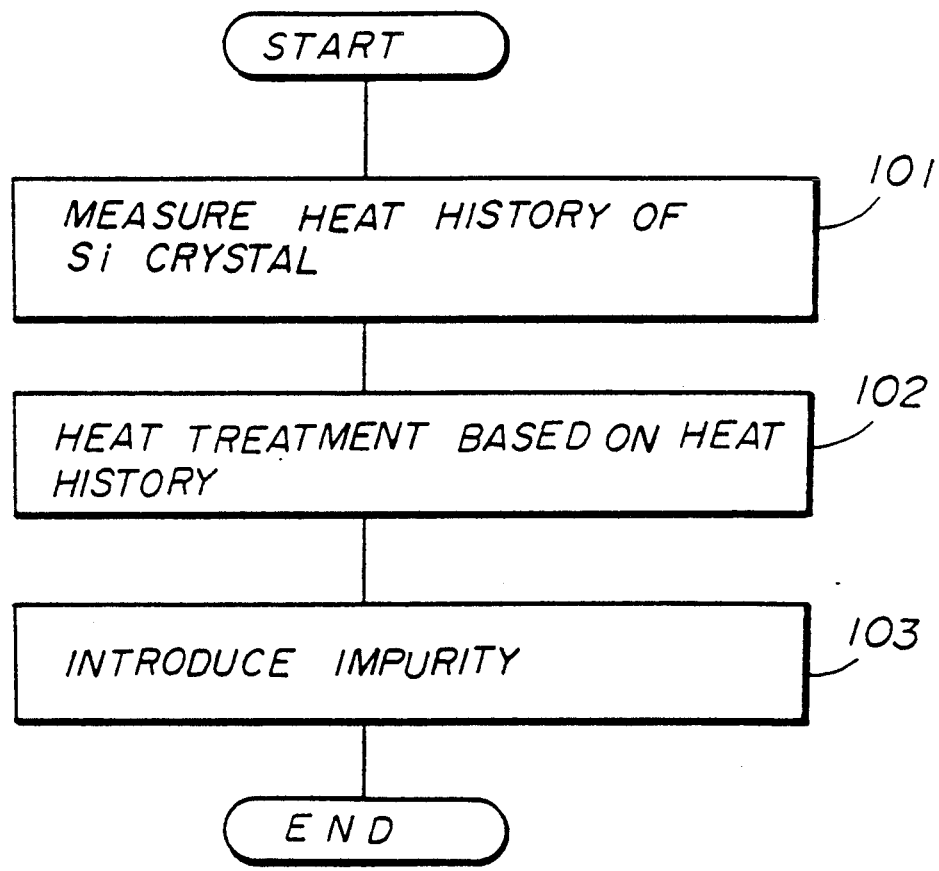
FIG. 12 is a flowchart illustrating a semiconductor device fabricating process according to a preferred embodiment of the present invention.

Referring to FIG. 12, the thermal histories of silicon crystals (wafers) sliced from the same ingot are measured according to the aforementioned silicon crystal evaluation method (step 101). At step 102, a heat treatment is carried out for the silicon wafers so that all the wafers sliced from the same ingot have an identical thermal history. Thereby, all the silicon wafers sliced from the same silicon ingot have the same thermal history, so that subsequent device processing can be carried out on the same condition. At step 103, an impurity having a conduction type different from that of the silicon wafers is introduced into the silicon wafers. Thereby, a PN junction (diode) is obtained. This diode is the most simple semiconductor device. It will be noted that there is a variety of device processing. The silicon crystal evaluation method can be applied to a variety of device processing so that silicon wafers have almost the same thermal history and can be handled on the same device processing condition.

Figure 13:
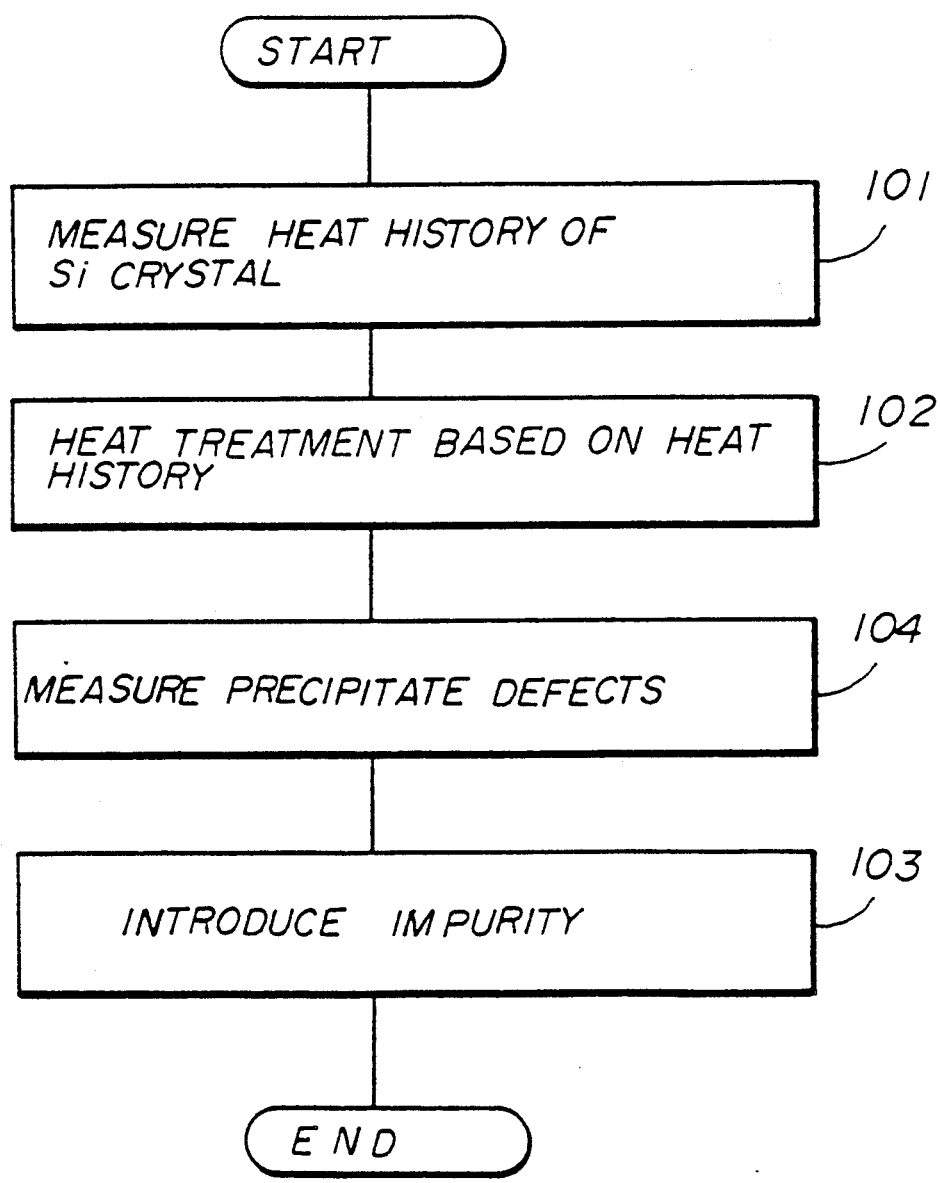
FIG. 13 is a flowchart illustrating a semiconductor device fabricating process according to another preferred embodiment of the present invention.

It is also possible to add step 104 to the procedure shown in FIG. 12, as shown in FIG. 13. At step 104, precipitate defects are evaluated according to the silicon crystal evaluation method. Thereby, it becomes possible to determine whether or not the heat treatment (step 102) based on the measurement results is appropriate. In actual device processing, some silicon crystals are extracted as samples, and step 104 is carried out for the extracted samples.

The present invention is not limited to the specifically disclosed embodiments, and variations and modifications may be made without departing from the scope of the present invention.

What is claimed is:

1. A silicon crystal evaluation method comprising the steps of:
    a) maintaining, at room temperature, a plurality of silicon crystals, each of said silicon crystals containing oxygen impurities, said silicon crystals including a silicon crystal having an unknown thermal history and reference silicon crystals having respective known thermal histories;
    b) determining an intensity of an oxygen impurity infrared absorption peak of each of said plurality of silicon crystals at a wavenumber of $1107 \pm 3$ cm$^{-1}$;
    c) decreasing said temperature of said plurality of silicon crystals equal to or lower than 10K;
    d) determining an intensity of an oxygen impurity infrared absorption peak of each of said silicon crystals at a predetermined wavenumber;
    e) determining a first peak intensity ratio between the intensity of the oxygen impurity infrared absorption peak of each of said silicon crystals at $1107 \pm$ cm$^{-1}$ and the intensity of the oxygen impurity infrared absorption peak of each of said silicon crystals at said predetermined wavenumber;
    f) increasing said temperature of said plurality of silicon crystals to change said oxygen impurities to isolated point lattice defects;
    g) determining an intensity of an oxygen impurity infrared absorption peak of each of said silicon crystals at said isolated point lattice defects;
    h) determining a second peak intensity ratio between the intensity of the oxygen impurity infrared absorption peaks of each of said silicon crystals at room temperature and the intensity of oxygen impurity infrared absorption peak of each of said silicon crystals at said isolated point lattice defects;
    i) obtaining a first difference between said first peak intensity ratio of said silicon crystal and a corresponding, second peak intensity ratio obtained when all oxygen impurities of said silicon crystal are isolated point lattice defects;
    j) obtaining a second difference between said first peak intensity ratio of each of said reference silicon crystals and said second peak intensity ratio of each of said reference silicon crystals obtained when all oxygen impurities are isolated point lattice defects; and
    k) determining the unknown thermal history of said silicon crystal from reference data which defines a relationship between said second difference and said known thermal histories.

2. A silicon crystal evaluation method as claimed in claim 1, wherein said step d) comprises the step of determining, at said temperature equal to or lower than 10K, an intensity of an oxygen impurity infrared absorption peak of each of said silicon crystals at a wavenumber of $1206 \pm 3$ cm$^{-1}$.

3. A silicon crystal evaluation method as claimed in claim 1, wherein said step d) comprises the step of determining, at said temperature equal to or lower than 10K, an intensity of an oxygen impurity infrared absorption peak of each of said silicon crystals at a wavenumber of $1749 \pm 3$ cm$^{-1}$.

4. A silicon crystal evaluation method as claimed in claim 1, wherein said step d) comprises the steps of:
    determining, at said temperature equal to or lower than 10K, an intensity of an oxygen impurity infrared absorption peak of each of said silicon crystals at a wavenumber of $1206 \pm 3$ cm$^{-1}$; and
    determining, at said temperature equal to or lower than 10K, an intensity of an oxygen impurity infrared absorption peak of each of said silicon crystals at a wavenumber of $1749 \pm 3$ cm$^{-1}$.

5. A silicon crystal evaluation method as claimed in claim 1, wherein said reference silicon crystals comprise silicon crystals which have been subjected to respectively different heat treatments.

6. A silicon crystal evaluation method as claimed in claim 1, further comprising the step of determining an intensity of an infrared absorption peak at about 1128 cm$^{-1}$ at a temperature equal to or lower than 10K.

7. A silicon crystal evaluation method as claimed in claim 6, wherein said step d) comprises the step of regulating a measurement temperature at said temperature equal to or lower than 10K based said infrared absorption peak at about 1128 cm$^{-1}$.

8. A silicon crystal evaluation method comprising the steps of:
    a) determining a crystal defect infrared absorption spectrum in a wavenumber range between 900 cm$^{-1}$ and 1300 cm$^{-1}$;

b) determining an intensity of an infrared absorption peak appearing at a predetermined wavenumber when oxygen impurities are isolated point lattice defects; and c) determining a concentration of isolated interstitial oxygen impurities based on an intensity of said crystal defect infrared absorption spectrum determined by said step a) and an intensity of said infrared absorption peak determined by said step b).

9. A silicon crystal evaluation method as claimed in claim 8, wherein said step b) comprises determining an intensity of an infrared absorption peak appearing at a wavenumber of $1206\pm2$ cm$^{-1}$ when oxygen impurities are isolated point lattice defects.

10. A silicon crystal evaluation method as claimed in claim 8, wherein said step b) comprises determining an intensity of an infrared absorption peak appearing at a wavenumber of $1749\pm2$ cm$^{-1}$ when oxygen impurities are isolated point lattice defects.

11. A silicon crystal evaluation method as claimed in claim 8, further comprising the step of determining precipitate defects based on a difference between the intensity of said infrared absorption peak determined by said step b) from the intensity of said infrared absorption peak determined by said step a).

12. A silicon crystal evaluation method as claimed in claim 8, wherein said step c) comprises the step of multiplying the intensity of said infrared absorption peak determined by said step b) by a predetermined coefficient.

13. A silicon crystal evaluation method as claimed in claim 8, wherein:

said step a) determines the crystal defect infrared absorption spectrum in the wavenumber range between 900 cm$^{-1}$ and 1300 cm$^{-1}$ at room temperature; and said step b) determines the intensity of the infrared absorption peak appearing at the predetermined wavenumber when oxygen impurities are isolated point lattice defects at a temperature equal to or lower the 10K.

14. A semiconductor device fabrication method comprising the steps of:

a) determining a thermal history of a silicon wafer;

b) heating said silicon wafer based on said thermal history determined by said step a); and c) introducing an impurity having a conduction type opposite to that of said silicon wafer into said silicon wafer so that a PN-type junction is formed in said silicon wafer, wherein said step a) comprises:

a-1) maintaining, at room temperature, and determining an intensity of an oxygen impurity infrared absorption peak of each of a plurality of silicon crystals at a wavenumber of $1107\pm3$ cm$^{-1}$, each of said silicon crystals containing oxygen impurities, said silicon crystals including said silicon wafer having an unknown thermal history and reference silicon crystals having respective known thermal histories;

a-2) decreasing a temperature equal to or lower than 10K and determining an intensity of an oxygen impurity infrared absorption peak of each of said silicon crystals at a predetermined wavenumber;

a-3) determining a first peak intensity ratio between the intensity of the oxygen impurity infrared absorption peak of each of said silicon crystals at $1107\pm^{-1}$ and the intensity of the oxygen impurity infrared absorption peak at said predetermined wavenumber;

a-4) determining a first difference between said first peak intensity ratio of said evaluation silicon crystal and a corresponding, second peak intensity ratio obtained when all oxygen impurities are isolated point lattice defects;

a-5) determining a second difference between said first peak intensity ratio of each of said reference silicon crystals and said second peak intensity ration of each of said reference silicon crystals when all oxygen impurities are isolated point lattice defects; and a-6) determining the unknown thermal history of said silicon crystal from reference data which defines a relationship between said second difference and said known thermal histories.

15. A semiconductor device fabrication method as claimed in claim 14, wherein said step a) further comprises the steps of:

a-7) determining a crystal defect infrared absorption spectrum in a wavenumber range between 900 cm$^{-1}$ and 1300 cm$^{-1}$;

a-8) determining an intensity of an infrared absorption peak appearing at a predetermined wavenumber when oxygen impurities are isolated point lattice defects;

a-9) determining a concentration of isolated interstitial oxygen impurities from an intensity of said crystal defect infrared absorption spectrum and the intensity of said infrared absorption peak determined by said step a-8); and a-10) determining precipitate defects based on a difference between the intensity of said infrared absorption peak determined by said step a-8) from the intensity of said infrared absorption peak determined by said step a-7).

16. A semiconductor device fabrication method as claimed in claim 15, wherein said step b) comprises the step of controlling said heating of said silicon wafer based on said precipitate defects determined by said step a-10).

17. A semiconductor device fabrication method as claimed in claim 15, wherein said steps a-7), a-8), a-9) and a-10) are carried out between said steps b) and c).

18. A semiconductor device fabrication method as claimed in claim 14, wherein said step a-2) comprises the step of decreasing said temperature equal to or lower than 10K, determining an intensity of an oxygen impurity infrared absorption peak of each of said silicon crystals at a wavenumber of $1206\pm3$ cm$^{-1}$.

19. A semiconductor device fabrication method as claimed in claim 14, wherein said step a-2) comprises the step of decreasing said temperature equal to or lower than 10K, determining an intensity of an oxygen impurity infrared absorption peak of each of said silicon crystals at a wavenumber of $1749\pm3$ cm$^{-1}$.

20. A semiconductor device fabrication method as claimed in claim 14, wherein said step a-2) comprises the steps of:

decreasing said temperature equal to or lower than 10K, and determining an intensity of an oxygen impurity infrared absorption peak of each of said silicon crystals at a wavenumber of $1206\pm3$ cm$^{-1}$; and determining an intensity of an oxygen impurity infrared absorption peak of each of said silicon crystals at a wavenumber of $1749\pm3$ cm$^{-1}$ at said temperature equal to or lower than 10K.

21. A semiconductor device fabrication method as claimed in claim 14, wherein said reference silicon crystals comprise silicon crystals which have been subjected to respectively different heat treatments.

22. A semiconductor device fabrication method as claimed in claim 15, wherein said step a-8) comprises determining an intensity of an infrared absorption peak appearing at a wavenumber of $1206\pm2$ cm$^{-1}$ when oxygen impurities are isolated point lattice defects.

23. A semiconductor device fabrication method as claimed in claim 15, wherein said step a-8) comprises determining an intensity of an infrared absorption peak appearing at a wavenumber of $1749\pm2$ cm$^{-1}$ when oxygen impurities are isolated point lattice defects.

24. A semiconductor device fabrication method as claimed in claim 15, wherein said step a-9) comprises the step of multiplying the intensity of said infrared absorption peak determined by said step a-8) by a predetermined coefficient.

25. A semiconductor device fabrication method as claimed in claim 15, wherein:
   said step a-7) determines the crystal defect infrared absorption spectrum in the wavenumber range between 900 cm$^{-1}$ and 1300 cm$^{-1}$ at room temperature; and
   said step a-8) determines the intensity of the infrared absorption peak appearing at the predetermined wavenumber when oxygen impurities are isolated point lattice defects at a temperature equal to or lower than 10K.

* * * * *